United States Patent
Li et al.

(10) Patent No.: US 10,441,397 B2
(45) Date of Patent: Oct. 15, 2019

(54) MEDICAL DEVICE AND METHOD FOR CONDUCTING A SURGERY THROUGH A BODY OPENING

(71) Applicant: Boston Scientific Scimed, Inc., Maple Grove, MN (US)

(72) Inventors: Jamie Li, Lexington, MA (US); Timothy P. Harrah, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 736 days.

(21) Appl. No.: 15/138,917

(22) Filed: Apr. 26, 2016

(65) Prior Publication Data

US 2016/0235513 A1   Aug. 18, 2016

Related U.S. Application Data

(63) Continuation of application No. 13/610,292, filed on Sep. 11, 2012, now Pat. No. 9,339,339.
(Continued)

(51) Int. Cl.
*A61B 46/17* (2016.01)
*A61B 46/00* (2016.01)
(Continued)

(52) U.S. Cl.
CPC ........ *A61F 2/0022* (2013.01); *A61B 17/0218* (2013.01); *A61B 17/0293* (2013.01);
(Continued)

(58) Field of Classification Search
CPC ......... A61B 46/17; A61B 46/30; A61B 17/42; A61B 1/303; A61B 1/307;
(Continued)

(56) References Cited

U.S. PATENT DOCUMENTS 1,120,549 A * 12/1914 Schellberg ......... A61M 25/0111
   206/364
4,043,328 A *  8/1977 Cawood, Jr. ........... A61B 46/30
   128/850
(Continued)

FOREIGN PATENT DOCUMENTS

| WO | 1995/07056 A2 | 3/1995 |
| WO | 2007/087470 A2 | 8/2007 |
| WO | 2013/040031 A1 | 3/2013 |

OTHER PUBLICATIONS

International Search Report and Written Opinion received for PCT Patent Application No. PCT/US2012/054860, dated Jan. 16, 2013, 11 pages.
(Continued)

*Primary Examiner* — David W Bates
(74) *Attorney, Agent, or Firm* — Brake Hughes Bellermann LLP

(57) ABSTRACT

A medical device and method for facilitating a surgery through a body opening is disclosed. The medical device includes a flexible member configured to be placed within the body opening so as to cover a portion of the body opening. The flexible member includes a distal end portion with a closed end, a proximal end portion with an open end and an elongate portion joining the proximal end portion and the distal end portion. The proximal end portion is configured to extend out of the patient's body opening to cover an area around and outside the patient's body opening.

5 Claims, 7 Drawing Sheets

Related U.S. Application Data

(60) Provisional application No. 61/535,617, filed on Sep. 16, 2011.

(51) Int. Cl.

| | | |
|---|---|---|
| *A61B 17/02* | (2006.01) | |
| *A61B 90/40* | (2016.01) | |
| *A61F 2/00* | (2006.01) | |
| *A61B 17/34* | (2006.01) | |
| *A61B 17/00* | (2006.01) | |

(52) U.S. Cl.
CPC .......... *A61B 17/3468* (2013.01); *A61B 46/17* (2016.02); *A61B 46/30* (2016.02); *A61B 17/3423* (2013.01); *A61B 90/40* (2016.02); *A61B 2017/00889* (2013.01); *A61B 2017/00951* (2013.01); *A61B 2017/0225* (2013.01)

(58) Field of Classification Search
CPC ..... A61B 2017/345; A61B 46/13; A61B 1/31; A61B 2017/00287; A61F 2002/0072; A61F 6/065; A61F 6/08; A61F 6/14; A61F 6/12; A61F 6/148; A61F 6/18
See application file for complete search history.

(56) References Cited

U.S. PATENT DOCUMENTS

| | | | |
|---|---|---|---|
| 4,581,028 A | 4/1986 | Fox, Jr. et al. | |
| 4,877,033 A * | 10/1989 | Seitz, Jr. ............ | A61B 1/00142 600/441 |
| 5,395,354 A * | 3/1995 | Vancaillie ................ | A61B 1/12 128/846 |
| 5,623,946 A * | 4/1997 | Hessel .................... | A61F 6/065 128/844 |
| 5,976,146 A | 11/1999 | Ogawa et al. | |
| 6,216,704 B1 | 4/2001 | Ingle et al. | |
| 6,589,167 B1 | 7/2003 | Shimomura et al. | |
| 7,316,233 B2 * | 1/2008 | Auerbach ............. | A61B 46/27 128/849 |
| 9,517,058 B2 * | 12/2016 | Harari ..................... | A61B 8/12 |
| 2002/0058674 A1 * | 5/2002 | Hedenstrom ........ | A61K 9/0014 514/292 |
| 2004/0015185 A1 | 1/2004 | Ewers et al. | |
| 2005/0061328 A1 * | 3/2005 | Reddy .................... | A61F 6/065 128/830 |
| 2006/0247498 A1 | 11/2006 | Bonadio et al. | |
| 2007/0023053 A1 * | 2/2007 | Bowen ................... | A61B 46/30 128/853 |
| 2009/0281456 A1 * | 11/2009 | Park ................. | A61B 17/00234 600/582 |
| 2010/0280523 A1 * | 11/2010 | Chen ....................... | A61B 1/31 606/110 |
| 2011/0022056 A1 * | 1/2011 | Haadem ................ | A61B 17/42 606/119 |
| 2011/0114698 A1 | 5/2011 | Baxter, III et al. | |
| 2011/0213309 A1 | 9/2011 | Young et al. | |
| 2012/0157779 A1 | 6/2012 | Fischvogt | |
| 2013/0072759 A1 | 3/2013 | Li et al. | |
| 2013/0131457 A1 * | 5/2013 | Seckin ............... | A61B 1/00087 600/235 |
| 2013/0225932 A1 * | 8/2013 | Smith .................... | A61B 1/313 600/206 |
| 2014/0303447 A1 * | 10/2014 | Singh .................... | A61B 1/0684 600/207 |
| 2016/0051399 A1 * | 2/2016 | Tang ...................... | A61F 6/065 128/830 |
| 2017/0014199 A1 * | 1/2017 | Schwartz ............... | A61B 46/30 |
| 2017/0224321 A1 * | 8/2017 | Kessler ............ | A61B 17/00234 |
| 2018/0132896 A1 * | 5/2018 | Begg ...................... | A61B 1/303 |

OTHER PUBLICATIONS

International Preliminary Report on Patentability received for PCT Patent Application No. PCT/US2012/054860, dated Mar. 18, 2014, 7 pages.
Restriction Requirement received for U.S. Appl. No. 13/610,292, dated Oct. 9, 2014, 6 pages.
Response to Restriction Action received for U.S. Appl. No. 13/610,292, filed Dec. 8, 2014, 1 page.
Non-Final Office Action received for U.S. Appl. No. 13/610,292, dated Dec. 26, 2014, 9 pages.
Response to Non-Final Office Action for U.S. Appl. No. 13/610,292, filed on Mar. 18, 2015, 7 pages.
Final Office Action received for U.S. Appl. No. 13/610,292, dated May 28, 2015, 12 pages.
Response to Final Office Action for U.S. Appl. No. 13/610,292, filed on Jul. 22, 2015, 7 pages.
Non-Final Office Action received for U.S. Appl. No. 13/610,292, dated Sep. 11, 2015, 6 pages.
Response to Non-Final Office Action for U.S. Appl. No. 13/610,292, filed on Dec. 9, 2015, 7 pages.
Notice of Allowance received for U.S. Appl. No. 13/610,292, dated Jan. 13, 2016, 5 pages.

* cited by examiner

MEDICAL DEVICE AND METHOD FOR CONDUCTING A SURGERY THROUGH A BODY OPENING

CROSS-REFERENCE TO RELATED APPLICATION

This application is a continuation of, and claims priority to, U.S. patent application Ser. No. 13/610,292, filed on Sep. 11, 2012, entitled "A MEDICAL DEVICE AND METHOD FOR CONDUCTING A SURGERY THROUGH A BODY OPENING", which, in turn, claims priority to, U.S. Provisional Application No. 61/535,617, filed Sep. 16, 2011, entitled "A MEDICAL DEVICE AND METHOD FOR CONDUCTING A SURGERY THROUGH A BODY OPENING", which is incorporated by reference herein in its entirety.

BACKGROUND

Field

The present invention generally relates to surgical devices and procedures, particularly devices and methods used for facilitating surgery through a body opening.

Description of the Related Art

Often, surgical devices, equipment, implants, or any other material passed through a body opening such as an ear, nose, mouth, throat, vagina, or rectum have a potential to carry undesirable contaminants such as biological organisms within a patient's body. These undesirable organisms may be pathogenic bacteria, viral particles, fungi, and the like, which can be carried during the course of a surgical procedure. These contaminants, if carried within the patient's body, may create severe complications. Therefore, surgeries require proper sterilization of a surgical field or a surgical site to ensure safety from these contaminants.

Various techniques have been developed for sterilization of the surgical field during a surgical procedure through the body opening. Existing sterilization techniques and devices involve use of disinfectants and sterile gloves. The disinfectants may kill most of the germs, bacteria, and similar organisms. The sterile gloves are used to reduce the contact of bare hands (that may carry harmful organisms) with the devices, equipment, implants, or any other material being used during the surgical procedure. The disinfectants and the sterile gloves may be used individually as well as together. However, it has been found that even after using the disinfectants and the gloves, the surgical devices, equipment, implants, or any other material passed within the body opening during the surgical procedure may contain these undesirable contaminants or organisms.

In accordance with the foregoing, there is a need for a device and a method for facilitating sterilization of the entire surgical field or site during the surgical procedure performed through the body opening.

SUMMARY

A medical device and method for facilitating a surgery through a body opening is disclosed. The medical device includes a flexible member configured to be placed within the body opening so as to cover a portion of the body opening. The flexible member includes a distal end portion with a closed end, a proximal end portion with an open end and an elongate portion joining the proximal end portion and the distal end portion. The proximal end portion is configured to extend out of the patient's body opening to cover an area around and outside the patient's body opening.

BRIEF DESCRIPTION OF THE FIGURES

The invention and the following detailed description of certain embodiments thereof may be understood by reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "operatively coupled," as used herein, is defined as connected, although not necessarily directly and mechanically.

The present invention relates to a medical device configured to be inserted into a patient's body opening for facilitating a surgical procedure. In an embodiment, the medical device may be used for maintaining sterilization during the surgery. For example, the medical device may be used to sterilize an inner surface of the body opening or an entire surgical field or site, including the inner surface of the body opening and an area adjacent the body opening. In some embodiments, the medical device may be used during implantation of bodily implants or grafts through a vaginal opening for the treatment of pelvic floor disorders.

The terms proximal and distal described in relation to various medical devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure of surgery through the patient's body orifice as described in the present invention. The term proximal refers to an area that is closest to the operator. The term distal refers to an area that is farthest from the operator. The patient referred here as a human female may be a male or any other mammal.

Figure 1:
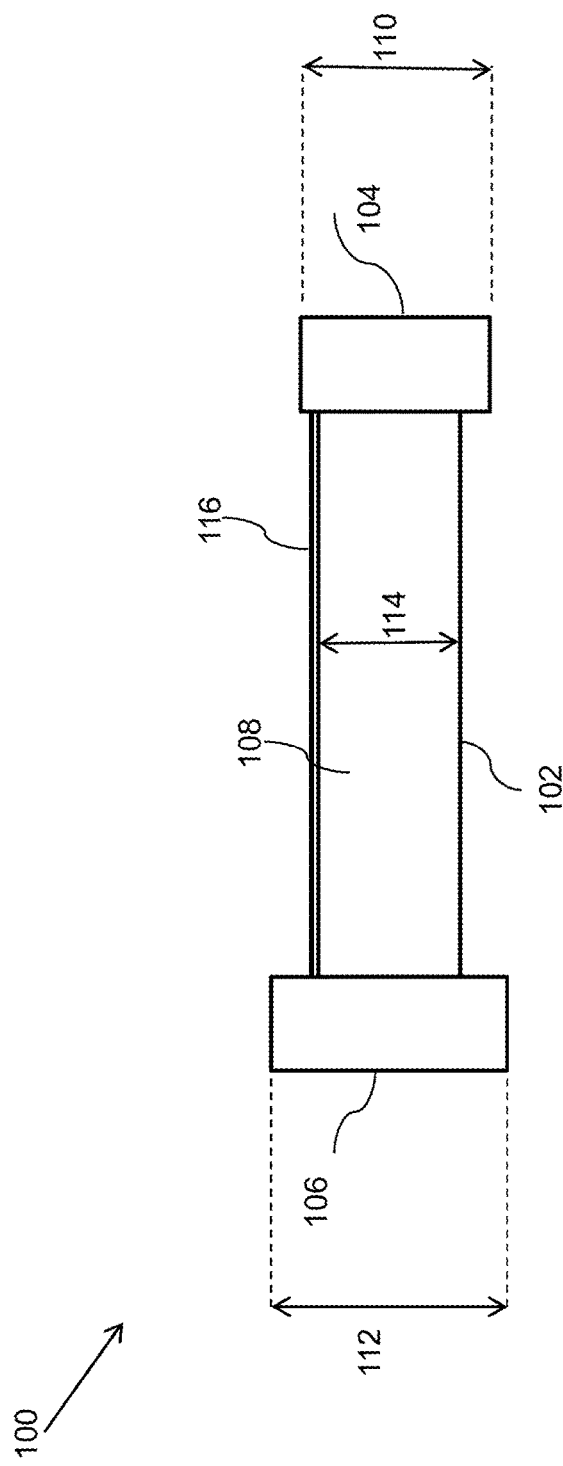
FIG. 1 illustrates a schematic diagram of a medical device for facilitating a surgical procedure through a patient's body opening, in accordance with an embodiment of the present invention.

FIG. 1 illustrates a medical device 100 for facilitating a surgical procedure conducted through a patient's body opening. In an embodiment of the present invention, the medical device 100 is utilized to help maintain sterility of a surgical field or a surgical site during the surgical procedure. The body opening can be a natural orifice or cavity such as an opening in the ear, nose, mouth, throat, vagina, rectum, and the like. In an embodiment of the present invention, the disclosed medical device 100 is configured to be used during implantation of a bodily implant or graft for the treatment of pelvic floor disorders in a human body. In such embodiments, the medical device 100 is configured to be inserted and placed within the vaginal opening.

The medical device 100 includes a flexible member 102 having a distal end portion 104, a proximal end portion 106 and an elongate portion 108. The flexible member 102 is hollow and is configured to receive surgical devices such as endoscopes, bodily implants, or the operator's hands. The flexible member 102 is configured to be placed within the body opening to cover a portion inside and outside the body opening. For example, a portion of the flexible member 102 may reside within the body opening and cover a surface therein, while the remainder portion may stay outside the body opening and cover a surface around and outside the body opening. The flexible member 102 includes an inner surface and an outer surface. The inner surface of the flexible member 102 is configured to come in contact with surgical devices or equipment and/or the operator's hand. The outer surface of the flexible member 102 is configured to come in contact with an inner surface of the body opening.

The distal end portion 104 of the flexible member 102 has a closed end. In some embodiments, the distal end portion 104 with the closed end has a substantially circular cross section. In some other embodiments, the distal end portion 104 can have an elliptical or any other shaped cross section. In an embodiment of the present invention, the distal end portion 104 includes a fixation mechanism. The fixation mechanism facilitates adherence of the closed end of the distal end portion 104 to the inner surface of the body opening. In some embodiments, the fixation mechanism is temporary so that the flexible member 102 can be detached from the inner surface of the body opening by decoupling the fixation mechanism. In an embodiment of the present invention, the fixation mechanism may include a ring-shaped element or a ring referred to as a first ring such that the first ring can directly come in contact with the inner surface of the body opening and facilitate adherence of the flexible member 102 therein. In some embodiments, the first ring is substantially circular at its cross section. The first ring holds the distal end portion 104 together with the inner surface of the body opening such that the flexible member 102 is appropriately attached. In an embodiment of the present invention, the outside surface of the flexible member 102 may contain an adhesive coating layer to contact and adhere to the inner surface of the body opening. In an embodiment of the present invention, the flexible member 102 may contain and release antimicrobials or antibiotics to further eliminate potential risk of infections.

The proximal end portion 106 of the flexible member 102 has an open end. In some embodiments, the proximal end portion 106 with an open end has a substantially circular cross section. In some other embodiments, the proximal end portion 106 can have an elliptical or any other cross section. In some embodiments, the shape of the proximal end portion 106 and the distal end portion 104 can be the same. In some other embodiments, the shape of the proximal end portion 106 and the distal end portion 104 are different.

The open end of the proximal end portion 106 provides an entrance to insert surgical instruments and bodily implants, or similar devices or materials within the hollow flexible member 102. In some embodiments, the proximal end portion 106 can include a ring referred to as a second ring. The second ring can directly come in contact with a body portion outside and around the body opening to facilitate adherence of the flexible member 102 therein. In some embodiments, the second ring is substantially circular at its cross section. In other embodiments, the second ring can have an elliptical or any other shaped cross section. In some embodiments, the second ring is similar to the shape of the first ring. In other embodiments, the shape of the second ring can be different from the first ring.

In some embodiments, the proximal end portion 106 of the flexible member 102 is configured to extend out of the body opening, thereby covering an area around and outside the body opening. For example, when the medical device 100 is placed within the body opening of the patient, the proximal end portion 106 of the medical device 100 may cover an area outside and around the body opening to help avoid any contact with an undesirable material or organism with the bodily implant (or any other material) or bodily tissues in the surgical field. In some embodiments, the proximal end portion 106 can be stretched or otherwise extended to cover an area outside and around the vaginal opening during placement of the bodily implants.

The elongate portion 108 of the flexible member 102 joining the proximal end portion 106 and the distal end portion 104 has a tubular shape. The elongate portion 108 is configured to be stretched or extended radially and longitudinally, and its shape can be adjusted for appropriate adherence and attachment with the body portion or the inner surface of the body opening when the medical device 100 is placed inside the body opening. In some embodiments, an outer surface of the elongate portion 108 can contact a portion of the inner surface of the body opening so as to help prevent the contacted portion of the inner surface from contamination. In some embodiments, the elongate portion 108 can be configured to take a shape in accordance with an anatomical structure of the inner portion of the body opening. For example, in cases where the medical device 100 is configured to be inserted into a vaginal opening, the elongate portion 108 can be configured to take a shape in accordance with the anatomical structure of the inner portion of the vaginal opening. In some embodiments, the elongate portion 108 can be configured to take a shape in accordance with the shape of outer surfaces of the anterior and posterior vaginal walls.

The medical device may employ several types of polymeric or/and biologic materials. For example, in some embodiments, the flexible member is composed of a polymeric material. Examples of polymeric material include natural rubber latex (NRL), polyethylene, polyurethane, polypropylene, and derivatives and mixtures thereof. In other embodiments, the flexible member is composed of a biologic material. Examples of biologic materials include bovine dermis, porcine dermis, porcine intestinal sub mucosa, bovine pericardium, a cellulose based product, cadaveric dermis, and the like. Also, in some embodiments, the first ring and the second ring of the flexible member may be made of a resilient material. The resilient material of the first ring and the second ring provides elasticity to the first ring and the second ring such that the resilient and elastic nature of the rings helps them fix on appropriate portions of the inner surface of the body opening by stretching. Therefore, the resilient material of the rings can be stretched for covering a desired contact area. Subsequently, the rings can regain their shape and be used to attach at other locations for adjustment purposes.

The distal end portion 104 has a size referred to as a first size 110, the proximal end portion 106 has a size referred to as a second size 112, and the elongate portion 108 has a size referred to as a third size 114. In some embodiments, the second size 112 is greater than the first size 110 and the third size 114. In some embodiments, the second size 112 is equal to the first size 110, but greater than the third size 114. In some other embodiments, the first size 110, the second size 112, and the third size 114 can be equal. In some embodiments, the first size 110, the second size 112, and the third size 114 can represent a first diameter, a second diameter, and a third diameter when cross sections of the distal end portion 104, proximal end portion 106, and the elongate portion 108 are circular.

In some embodiments, the medical device 100 further includes an adhesive 116 spread over a portion or throughout the outer surface of the flexible member 102. The adhesive 116 is spread over the outer surface of the flexible member 102 to enable its adherence to body portions such as the inner surface of the body opening and an area outside and surrounding the body opening. In an embodiment, the adhesive 116 is spread along the elongate portion 108 of the flexible member 102. In another embodiment, the adhesive 116 is spread over the outer surface of the elongate portion 108 and the distal end portion 104. In yet another embodiment, the adhesive 116 is spread over the entire outer surface of the flexible member 102, including the elongate portion 108, distal end portion 104, and the proximal end portion 106. The adhesive 116 facilitates proper placement or adherence of the flexible member 102 with the body portions. In some embodiments, the adhesive 116 also helps in sealing the flexible member 102 with the inner surface of the body opening. The adhesive, thus, keeps the flexible member 102 in place when it is pierced. For example, when the operator pierces the flexible member 102 to create an incision, the adhesive 116 ensures that the flexible member 102 or a portion of the flexible member 102 surrounding the pierced location is appropriately attached and sealed with the inner surface of the body opening and any foreign body or material or equipment does not come in contact with the inner surface.

In some embodiments, the medical device 100 may include a coating of an active agent to further enhance sterility of the surgical field during the surgical procedure. In some embodiments, the coating may be provided on the entire inner surface of the flexible member 102. In other embodiments, the coating may be provided only on a portion of the inner surface of the flexible member 102. In an embodiment of present invention, antimicrobial agents may be used as active agents in the coating. Antimicrobial agents useful for the practice of the present invention may include triclosan, chlorhexidine, nitrofurazone, benzalkonium chlorides, and silver protein; silver bromide, silver fluoride, silver lactate and silver nitrate; as well as other sources of silver ions including silver-based ion-exchange materials, and the like.

In another embodiment of the present invention, antiviral agents may be used as active agents in the coating. Antiviral agents useful for the practice of the present invention may include amantadines, rimantadines, ribavirins, idoxuridines, vidarabines, trifluridines, acyclovirs, ganciclovirs, zidovudines, foscarnets, interferons their homologs, analogs, fragments, derivatives, pharmaceutical salts and mixtures thereof.

In yet another embodiment of the present invention, antifungal agents may be used as active agents in the coating. Antifungal agents useful for the practice of the present invention may include Dapsone, Fluconazole, Flucytosine, Griseofulvin, Itraconazole, Ketoconazole, Miconazole KI, Amphotericin B, Carbol-Fuchsin, Ciclopirox, Clotrimzole, Econazole, Haloprogin, Mafenide, Miconazole, Naftifine, Nystatin, Oxiconazole, Silver Sulfadiazine, Sulconazole, Terbinafine, Tioconazole, Tolnafiate, Undecylenic acid, Butoconazle, Clotrimazole, Econazole, Gentian Violet, Miconazole, Nystatin, Terconazole, and Tioconazole.

In accordance with other embodiments, various types of active agents having specific sterilizing properties may be used for coating on the inner surface of the flexible member 102.

In some embodiments, the medical device 100 may further include a coating of a bio-compatible lubricant. The coating of the bio-compatible lubricant is applied at the inner surface of the flexible member 102. The coating of the bio compatible lubricant allows an easy passage of the bodily implant, surgical instruments, or similar devices through the body opening such as the vaginal opening.

Figure 2:
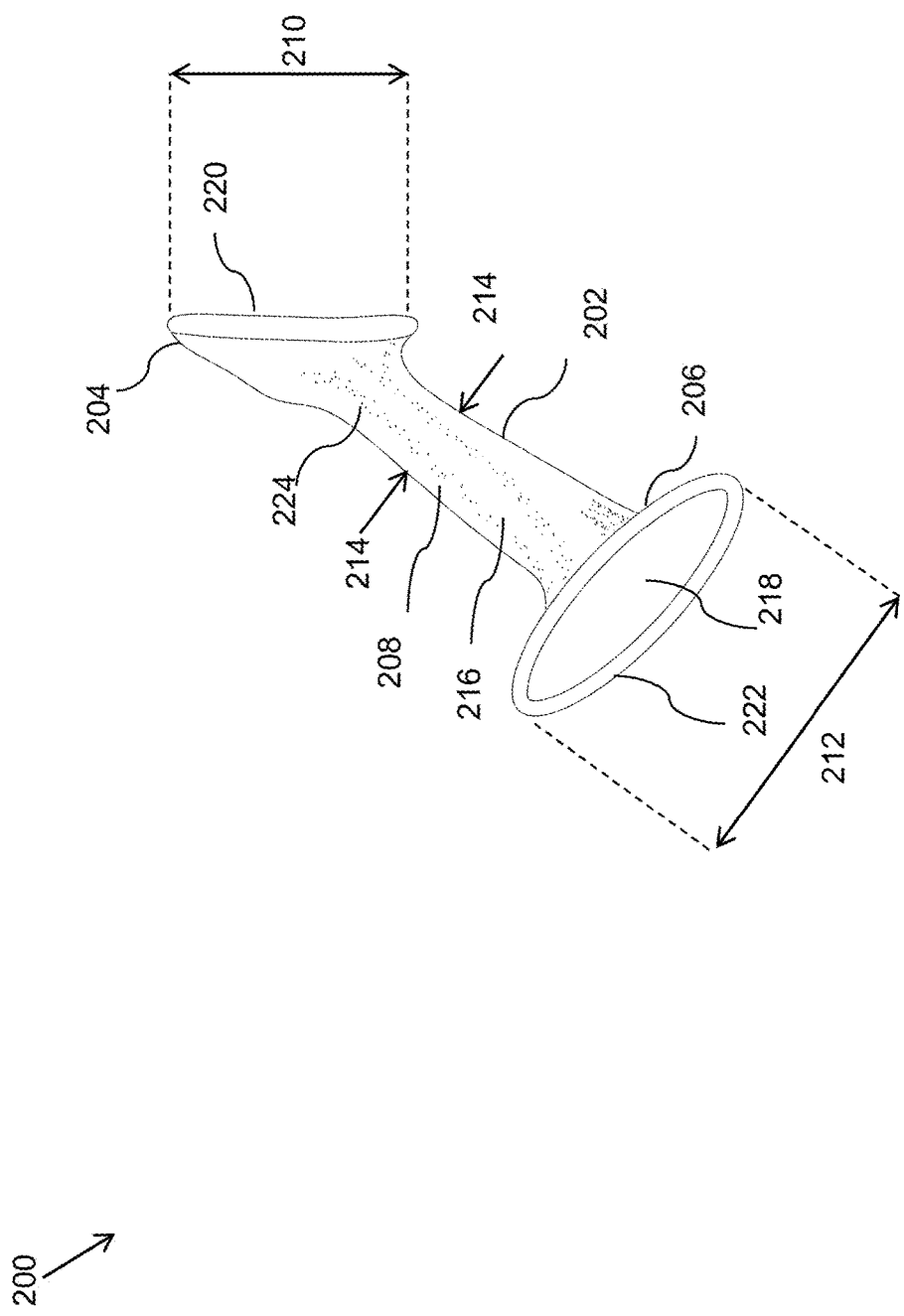
FIG. 2 illustrates a perspective view of a medical device for facilitating a surgical procedure through a patient's body opening, in accordance with an embodiment of the present invention.

FIG. 2 illustrates a perspective view of a medical device 200 configured to be inserted into a patient's body opening during a surgical procedure. The medical device 200 includes a flexible member 202. As illustrated, the flexible member 202 has a distal end portion 204, a proximal end portion 206, and an elongate portion 208 extending from the distal end portion 204 to the proximal end portion 206. The flexible member 202 includes an outer surface 216 and an inner surface 218.

The distal end portion 204 of the flexible member 202 has a closed end. In some embodiments, the distal end portion 204 with the closed end has a substantially circular cross section. In some other embodiments, the distal end portion 204 can have an elliptical or any other cross section. In an embodiment of the present invention, the distal end portion 204 includes a fixation mechanism, which facilitates adherence of the closed end of the distal end portion 204 to an inner surface of the body opening. In some embodiments, the fixation mechanism is temporary so that the flexible member 202 can be detached from the inner surface of the body opening by decoupling the fixation mechanism. As illustrated in FIG. 2, the fixation mechanism includes a ring-shaped element or a ring referred to as a first ring 220 such that the first ring 220 can directly come in contact with a body portion and facilitate adherence of the flexible member 202 therein. The first ring 220 is substantially circular at its cross section. In other embodiments, the first ring 220 can have an elliptical or any other cross section. The first ring 220 holds the distal end portion 204 together with the body portion such that the flexible member 202 is appropriately attached to the body portion.

As illustrated, in some embodiments, a central axis of the distal end portion 204 passing through the center of the distal end portion 204 is inclined by an angle to a central axis of the elongate portion 208 passing through the center of the elongate portion 208. The angle of inclination may be specified or configured to suit the surgical requirements and the anatomy of a specific patient. The angle of inclination is illustrated as the angle Ø in FIG. 3.

Referring again to FIG. 2, the proximal end portion 206 of the flexible member 202 has an open end. The open end of the proximal end portion 206 has a substantially circular cross section. The open end of the proximal end portion 206 provides an entrance to insert surgical instruments and bodily implants, or similar devices within the hollow flexible member 202. The proximal end portion 206 includes a ring referred to as a second ring 222. The second ring 222 can directly come in contact with a body portion outside and around the body opening to facilitate adherence of the second ring 222 therein. As shown in FIG. 2, the second ring 222 is substantially circular at its cross section. In other embodiments, the second ring 222 can have an elliptical or any other cross section. In some embodiments, as discussed in more detail below, an adhesive coating is disposed on the outside surface of the device. In such embodiment, the device may or may not include the ring 222.

The proximal end portion 206 of the flexible member 202 is configured to extend or stretch out of the body opening, thereby covering an area around and outside the body opening. For example, when the medical device 200 is placed within the body opening of the patient, the proximal end portion 206 of the medical device 200 covers an area outside and around the body opening to help avoiding any contact of unwanted material or organisms with a bodily implant or bodily tissues in the surgical field. In some embodiments, the proximal end portion 206 can be stretched to cover an area outside and around the vaginal opening during placement of the bodily implants for the treatment of pelvic floor disorders.

As illustrated, the elongate portion 208 of the flexible member 202 extends from the distal end portion 204 to the proximal end portion 206. The elongate portion 208 of the flexible member 202 has a tubular shape that is hollow from inside and its outer surface is configured to come in contact with the inner surface of the body opening. The elongate portion 208 is configured to be stretched or extended radially and longitudinally and its shape can be adjusted when the medical device 200 is placed inside the body opening for appropriate adherence and attachment to the body portion or the inner surface of the body opening. The elongate portion 208 can be configured to take a shape in accordance with an anatomical structure of the inner surface of the body opening. For example, in cases where the medical device 200 is configured to be inserted into a vaginal opening, the elongate portion 208 can be configured to take a shape in accordance with the anatomical structure of the inner surface of the vaginal opening.

In some embodiments, the flexible member 202 or a portion of the flexible member 202 such as the first ring 220 and the second ring 222 may be stretched or extended using a sterile gloved hand. In other embodiments, the flexible member 202 or a portion of the flexible member 202 such as the first ring 220 and the second ring 222 may be stretched or extended using a balloon catheter.

As described above, the flexible member 202 includes the outer surface 216 and the inner surface 218. The outer surface 216 of the flexible member 202 is coated with an adhesive 224. In some embodiments, the adhesive 224 is spread partially on an outer surface of the elongate portion 208. In other embodiments of the present invention, the adhesive 224 is spread completely and evenly over the entire outer surface of the elongate portion 208. Further, in other embodiments of the present invention, the adhesive 224 is spread at the entire outer surface 216 of the flexible member 202 including its distal end portion 204, elongate portion 208, and proximal end portion 206. In some embodiments, the adhesive 116 also helps in sealing the flexible member 102 with the inner surface of the body opening. The adhesive, thus, keeps the flexible member 102 in place when it is pierced. For example, when the operator pierces the flexible member 102 to create an incision, the adhesive 116 ensures that the flexible member 102 or a portion of the flexible member 102 surrounding the pierced location is appropriately attached and sealed with the inner surface of the body opening and any foreign body or material or equipment does not come in contact with the inner surface.

The inner surface 218 of the flexible member 202 may include a coating of an active agent to further enhance sterility of the body opening during the surgical procedure. In some embodiments, the coating may be provided on the entire inner surface 218 of the flexible member 202. In other embodiments, the coating may be provided only on a portion of the inner surface 218 of the flexible member 202. In an embodiment of the present invention, antimicrobial agents may be used as active agents in the coating. In another embodiment of the present invention, antiviral agents may be used as active agents in the coating. In yet another embodiment of the present invention, antifungal agents may be used as active agents in the coating. In accordance with other embodiments, various types of active agents having specific sterilizing properties may be used for coating on the inner surface 218 of the flexible member 202.

In some embodiments, the medical device 200 may further include a coating of a bio-compatible lubricant. The coating of the bio compatible lubricant is applied on the inner surface 218 of the flexible member 202. The coating of the bio-compatible lubricant allows an easy passage of the bodily implant, surgical instruments, or similar devices or materials through the body opening such as a vaginal opening.

As illustrated, the distal end portion 204 has a size referred to as a first size 210, the proximal end portion has a size referred to as a second size 212, and the elongate portion has a size referred to as a third size 214. As illustrated in FIG. 2, the second size 212 is greater than the first size 210 and the third size 214. The increased dimension of the proximal end portion 206 facilitates stretching of the proximal end portion 206 toward an external periphery and around the body opening such as the vaginal opening. Therefore, the proximal end portion 206 can safely cover an appropriate and desired area around the vaginal opening and helps preventing contamination therein.

The illustrated embodiment of the medical device 200 is configured to be placed inside the vaginal opening for the treatment of pelvic floor disorders. Accordingly, the medical device 200 is designed in conformation to the anatomical structure of the vaginal opening. However, it must be appreciated that various other designs of the medical device 200 and the flexible member 202 are possible and they can be configured to be placed in other body openings as well such as ear, nose, mouth, throat, anus, rectum, and the like. Accordingly, the length of the flexible member 202 and its various portions (distal 204, proximal 206, and elongate 208) is provided in accordance with the depth and anatomy of the particular body opening to be operated.

Figure 3:
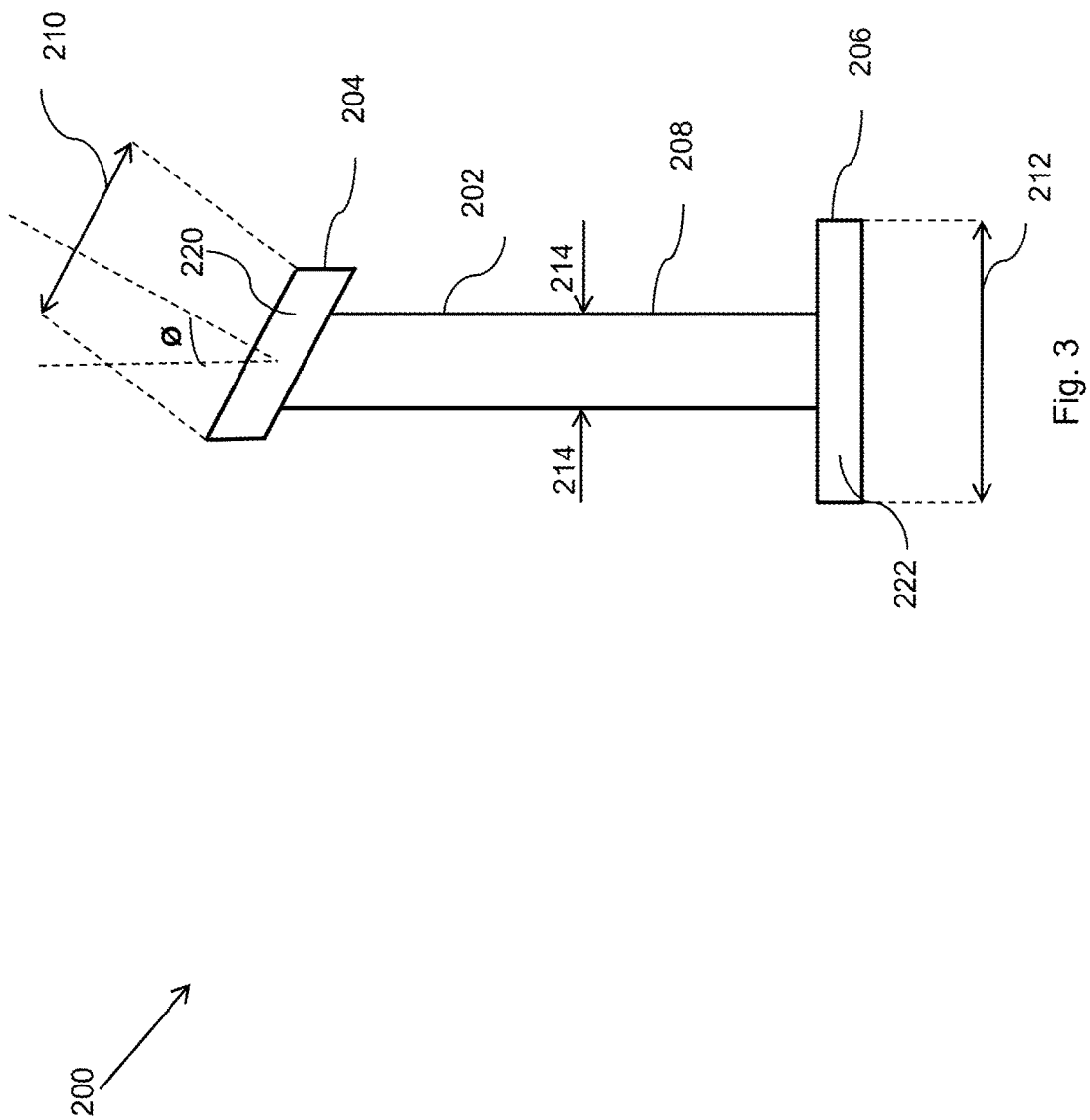
FIG. 3 illustrates a front view of the medical device of FIG. 2, in accordance with an embodiment of the present invention.

FIG. 3 illustrates a front view of the medical device depicted in FIG. 2. As illustrated and discussed above, with respect to the perspective view of FIG. 2, the flexible member 202 includes the proximal end portion 206, distal end portion 204, and the elongate portion 208. The second size 212 is substantially greater than the first size 210 and the third size 214. Also, in some embodiments, the first ring 220 is inclined with respect to the second ring 222 (or the elongate portion 208). For example, in some embodiments, the first ring 220 may be inclined by an angle Ø.

Figure 4:
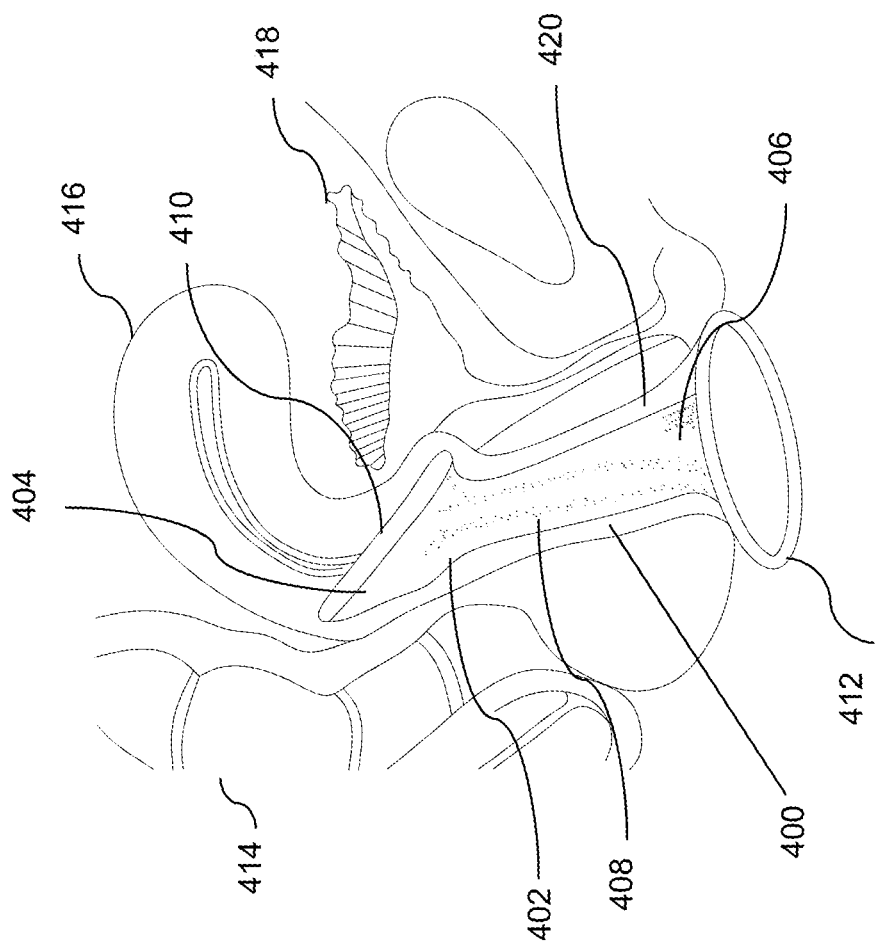
FIG. 4 illustrates placement of a medical device in a patient's vaginal opening for facilitating a surgical procedure, in accordance with an embodiment of the present invention.
Figure 5:
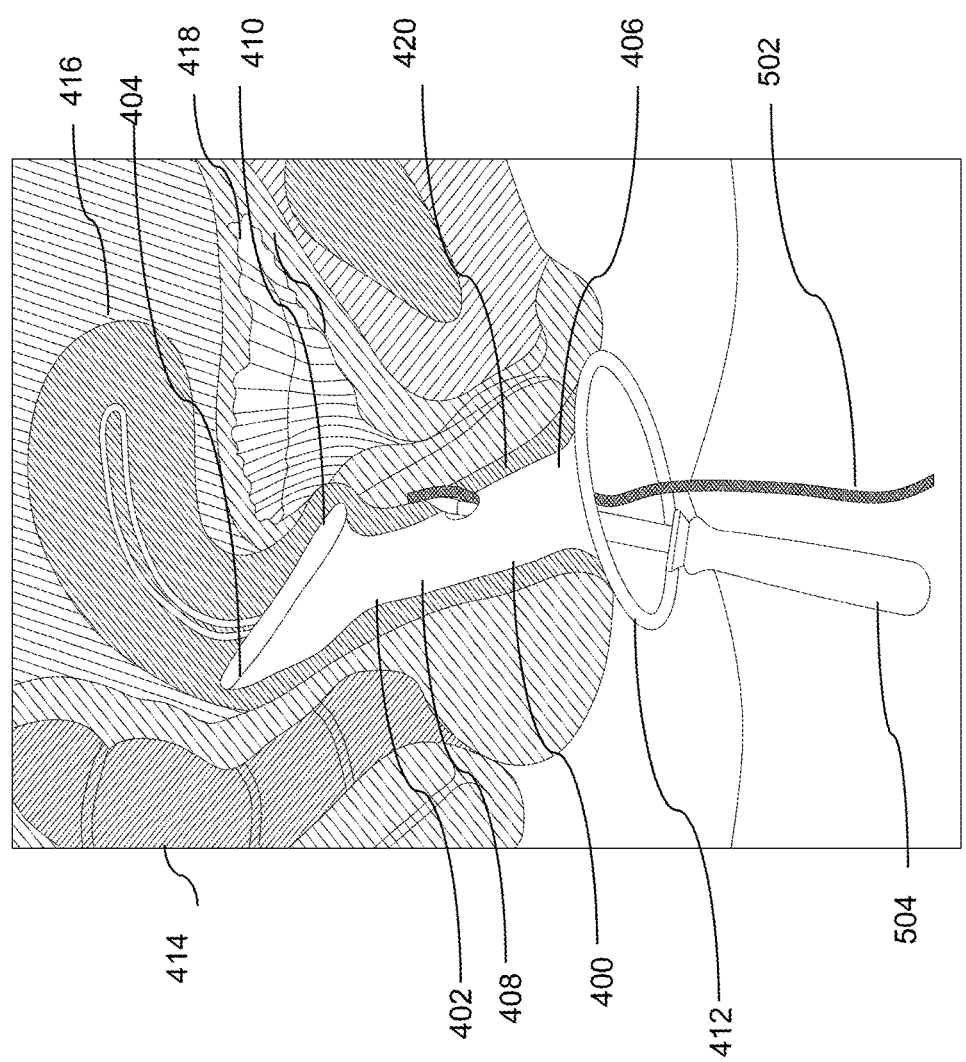
FIG. 5 illustrates delivery of a bodily implant in a patient's vaginal opening through a medical device, in accordance with an embodiment of the present invention

FIG. 4 illustrates placement of a medical device 400 in a patient's body opening, in accordance with an embodiment of the present invention. The medical device 400 includes a flexible member 402. The flexible member 402 includes a distal end portion 404, a proximal end portion 406, and an elongate portion 408. The distal end portion 404 includes a temporary fixation mechanism. In an embodiment, the temporary fixation mechanism has a ring referred to as a first ring 410. The proximal end portion 406 of the flexible member 402 has an open end. In an embodiment, the proximal end portion 406 includes a ring referred to as a second ring 412. The body portions of the patient such as a rectum 414, a uterus, 416, a vagina 420, and a urinary bladder 418 are also illustrated in FIG. 4. As shown, the flexible member 402 is placed inside the vagina 420 of the patient. The ring-shaped temporary fixation mechanism (first ring 410) coupled to the distal end portion 404 of the flexible member 402 is attached to an inner surface of the vagina 420 near the uterus 416. The elongate portion 408 of the flexible member 402 is in contact with outer surfaces of vaginal walls. The proximal end portion 406 of the medical device 400 extends out of the vagina 420 and covers an area around and outside the vaginal opening 420. In accordance with various embodiments, the flexible member 402 can be configured to cover an entire portion within the vaginal opening 420 (entire vulva) to help protect the surgical field from any foreign contamination. As discussed above also, in some embodiments, the medical device 400 may be placed in the patient's body for delivering a bodily implant such as shown in FIG. 5. FIG. 5 illustrates delivery of a bodily implant 502 through the medical device 400 in a patient's body opening, in accordance with an embodiment of the present invention. A piercing needle 504 for piercing the flexible member 402 at a desired location is also shown. The bodily implant 504 is placed at a desired location within the body opening via the incision created through the flexible member 402. The bodily implant 502 facilitates treatment of pelvic organ prolapse by providing a support to the prolapsed organ. The bodily implant 502 may be a sling, a mesh based device, and the like. In some embodiments, the body implant may be secured with specific tensions at posterior and anterior walls of the prolapsed organ to provide a support thereto.

Figure 6:
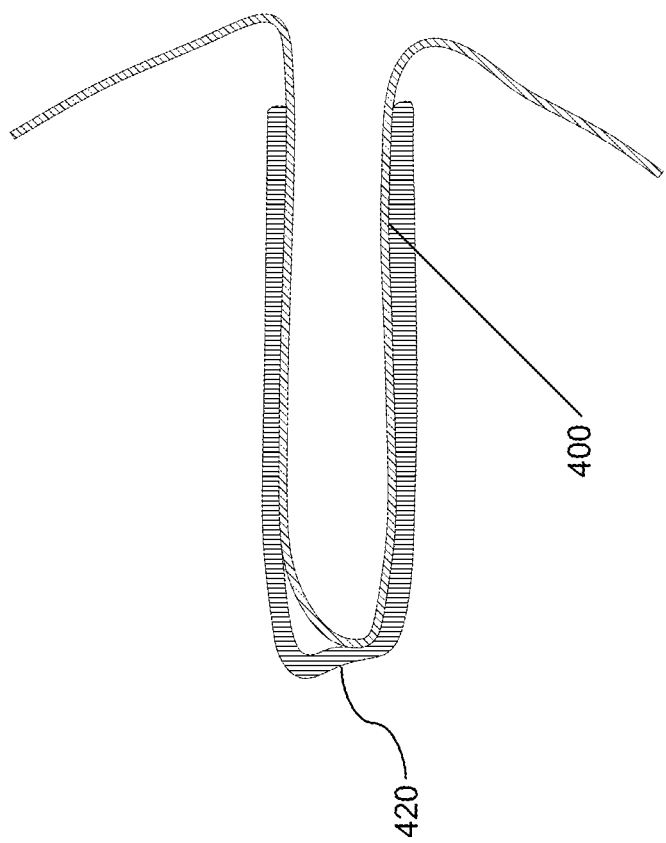
FIG. 6 illustrates a cross-sectional view of a medical device covering a patient's entire vulva, in accordance with an embodiment of the present invention.

In some embodiments, the flexible member may cover an entire portion of the vulva to help avoid contamination in the entire surgical field. FIG. 6 illustrates a cross-sectional diagram showing covering of a patient's entire vulva by the flexible member.

Figure 7:
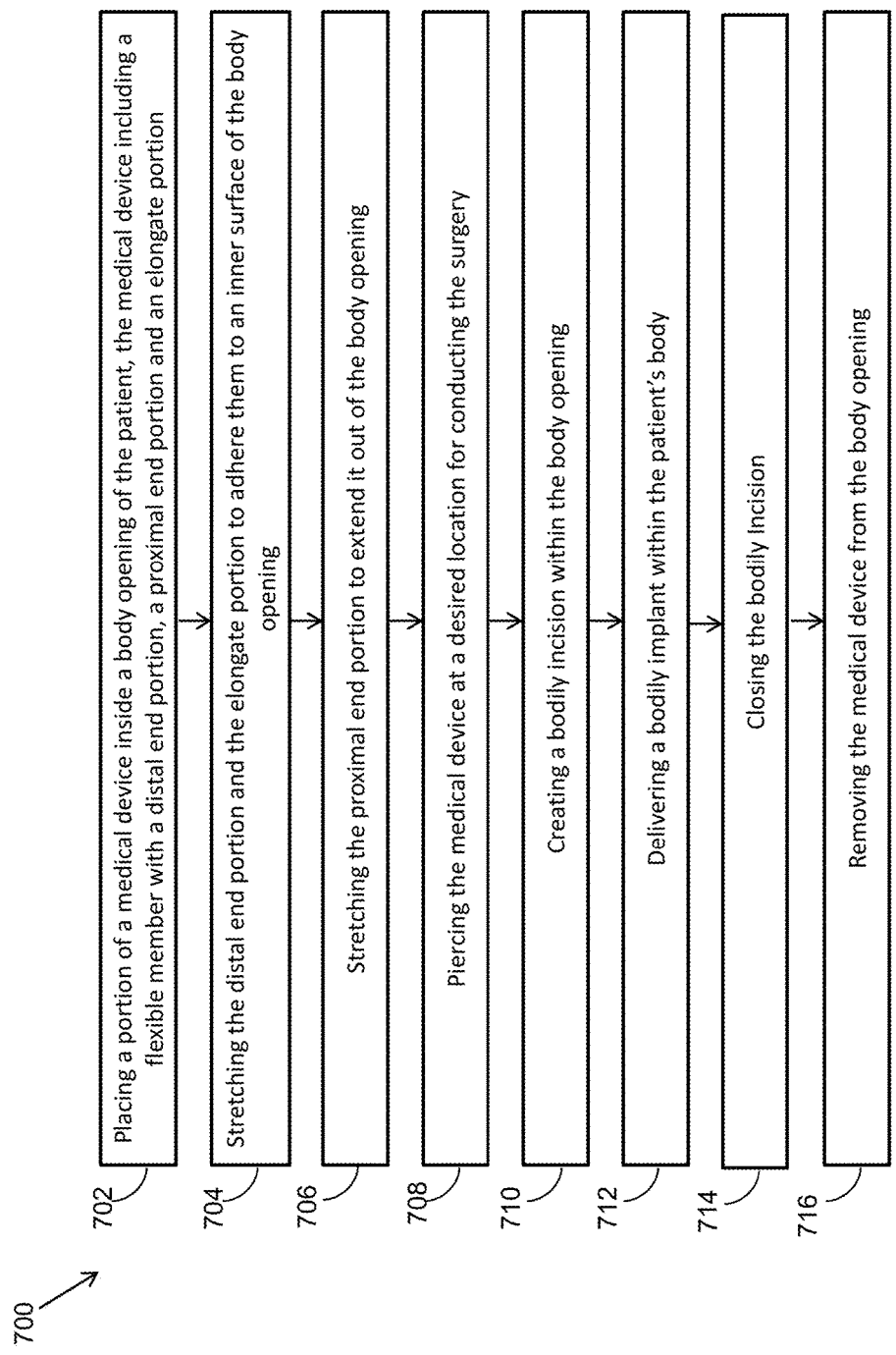
FIG. 7 is a flowchart illustrating a method of conducting a surgery, in accordance with an embodiment of the present invention.

Referring now to FIG. 7 in conjunction with FIGS. 4, 5 and 6, a method 700 for conducting a surgery using the medical device 400 is described in accordance with an embodiment of the present invention. The medical device 400 is hereafter used to describe the surgery in an exemplary embodiment. However, in certain other embodiments, other medical devices such as the medical device 100, the medical device 200 may also be employed.

The method 700 includes placing a portion of the medical device 400 inside the body opening of the patient at step 702. The body opening is a natural orifice. In an embodiment of the present invention, the body opening may be the vaginal opening 420. In other embodiments, the body opening can be an ear, nose, mouth, throat, rectum, and the like. In some embodiments, a portion of the medical device 400 resides outside the body opening such that it can surround the opening at its external periphery. For example, the distal end portion 404 and the elongate portion 408 can be placed inside the body opening while the proximal end portion 406 resides outside the opening 420. In still other embodiments, only the second ring 412 provided at the proximal end portion 406 resides outside, while the rest of the proximal end portion 406 is placed inside the opening.

The method further includes stretching the distal end portion 404 and the elongate portion 408 of the flexible member 402 at step 704 so as to facilitate the adherence of the medical device to the inner surface of the body opening. In some embodiments, the stretching can be done radially to allow the outer surface of the flexible member 402 adhere to the inner surface of the vaginal opening 420. In some other embodiments, the stretching can be done longitudinally also to allow the flexible member 402 to cover an entire length of the inner surface of the vaginal opening 420. The distal end portion 404 includes the fixation mechanism for facilitating the adherence of the closed end of the distal end portion 404 to the inner surface of the body opening. The fixation mechanism has the first ring 410 such that on stretching the distal end portion 404, the first ring 410 stretches and contacts body locations near the uterus over a large surface.

The method further includes stretching the proximal end portion 406 of the flexible member 402 at step 706 so that the proximal end portion 406 of the flexible member 402 extends out of the body opening and covers an area outside and around the body opening. In some embodiments, the stretching can be done longitudinally to allow the extension of the proximal end portion 406 out of the body opening. In some other embodiments, the stretching can be done radially also to allow the proximal end portion 406 to cover an entire area around the body opening.

In some embodiments, the medical device may include an adhesive spread over a portion or throughout the outer surface of the flexible member 402. The adhesive spread over the outer surface of the flexible member 402 facilitates its adherence to body portions such as the inner surface of the body opening and an area outside and surrounding the body opening. The method may include fixing the flexible member to the body portions with the use of the adhesive for ensuring proper adherence of the outer surface of the flexible member 402 at appropriate locations inside the body opening. The adhesive facilitates proper placement or adherence of the flexible member 102 with the body portions.

Once the medical device 400 is placed and adhered to inside the body opening, the medical device 400 is pierced at a desired location at step 708 for conducting the surgical procedure. In accordance with various embodiments, the medical device 400 may be pierced using the piercing needle 504 which may be a surgical needle, piercing knife, or similar devices.

In some embodiments, the adherence of the flexible member 402 may involve sealing of the inner surface of the body opening by the flexible member 402 using an adhesive. The adhesive, keeps the flexible member 102 in place when it is pierced. For example, when the operator pierces the flexible member 102, the adhesive ensures that the flexible member 402 or a portion of the flexible member 402 surrounding the pierced location is appropriately attached and seals the inner surface of the body opening from any foreign body or material or equipment.

In some embodiments, thereafter, a bodily incision is created within the body opening at step 710 through the pierced medical device 400. Further, in an embodiment, the body incision may be dilated using incision tools or dilators if required. For example, if the bodily implant requires more space than the width of the incision, the operator may dilate the body incision to provide enough space.

Subsequently, the bodily implant 502 is delivered within the body opening at step 712. The bodily implant 502 is delivered through the pierced portion of the medical device 400 and through the incision within the body opening. The bodily implant 502 facilitates treatment of different types of prolapsed organ by providing support to the prolapsed organ. The bodily implant 502 may be a sling, a mesh based device, or the like. In some embodiments, the body implant 502 may be secured with specific tensions at posterior and anterior walls of the prolapsed organ to provide a support thereto.

The bodily incision is closed at step 714. The bodily incision may be closed using a suitable closure technique such as stitching, clamping, suturing, or the like. The medical device 400 is removed from within the body opening at step 716 after the surgical procedure is completed.

In accordance with the described embodiment, an incision is made to perform the surgical procedure. In some embodiments, the medical device described above may be used in conjunction with endoscopic guidance or other similar systems providing visualization of the surgical field. The endoscope or any other similar device for visualization may be inserted within the body opening through the medical device 400 and examine interior of the body opening to accurately fix the flexible member 402 and create an incision through it. The endoscope may also include a light delivery system to illuminate the interior of the opening.

In some embodiments, a medical device is configured to be inserted into a patient's body opening for facilitating a surgery. The medical device includes a flexible member. The flexible member is configured to be placed within the body opening so as to cover a portion of the body opening. The flexible member includes a distal end portion with a closed end, a proximal end portion with an open end, the proximal end portion is configured to extend out of the patient's body opening to cover an area around the patient's body opening, and an elongate portion joining the proximal end portion and the distal end portion.

In some embodiments, the medical device is configured to sterilize a surgical field during the surgery. In some embodiments, the flexible member is made of a polymeric material. In some embodiments, the distal end portion includes a fixation mechanism configured to expand and fix temporarily inside the body orifice. In some embodiments, the fixation mechanism includes a ring. In some embodiments, the proximal end portion includes a ring configured to be stretched out of the body opening.

In some embodiments, the device further includes an adhesive provided on a portion of the flexible member contacting an inner surface of the body opening. The adhesive is configured to facilitate adherence of the flexible member on the inner surface of the body opening. In some embodiments, the flexible member is coated with an active agent for enhancing sterility of the flexible member. In some embodiments, the active agent is an antimicrobial agent. In some embodiments, the active agent is an antiviral agent. In some embodiments, the active agent is an antifungal agent.

In some embodiments, the device includes a coating with a biocompatible lubricant for facilitating passage of the medical device inside the body opening.

In some embodiments, a method for conducting a surgery through a body opening of a patient, the method includes placing a portion of a medical device inside the body opening, the medical device including a distal end portion with a closed end, a proximal end portion with an open end, and an elongate portion joining the proximal end portion and the distal end portion, wherein the distal end portion and the elongate portion contacts an inner surface of the body opening and the proximal end portion resides out of the body opening upon placement; and piercing the medical device at a desired location for conducting the surgery.

In some embodiments, the method includes stretching the distal end portion and the elongate portion so that the medical device adheres to the inner surface of the body opening.

In some embodiments, the method includes stretching the proximal end portion of the medical device so that it extends out of the patient's body opening to cover an area outside and around the patient's body opening.

In some embodiments, the method includes creating a bodily incision within the body opening through the medical device. In some embodiments, the method includes delivering a bodily implant to a location within the patient's body through the pierced location formed in the medical device. In some embodiments, the method includes closing the bodily incision. In some embodiments, the method includes removing the medical device from the body opening after completing the surgery.

In some embodiments, a method for conducting an implant surgery through a vaginal opening of a patient includes placing a portion of a medical device inside the vaginal opening, the medical device including a flexible member having a distal end portion with a closed end, a proximal end portion with an open end, and an elongate portion joining the proximal end portion and the distal end portion, wherein the distal end portion and the elongate portion contacts outer surfaces of vaginal walls and the proximal end portion resides out of the vaginal opening upon placement; piercing the medical device at a desired location for conducting the implant surgery; and delivering a bodily implant within the patient's body through the pierced location formed in the medical device.

In some embodiments, the implant surgery is performed for the treatment of pelvic organ prolapse. In some embodiments, the method includes covering an entire vulva of a patient's body with the flexible member before piercing the medical device. In some embodiments, the method includes fixing the flexible member onto the outer surfaces of the vaginal walls using an adhesive provided on an outer surface of the flexible member such that the adhesive allows adherence of the flexible member with the outer surfaces of the vaginal walls.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A method for conducting an implant surgery through a vaginal opening of a patient, the method comprising:

placing a portion of a medical device inside the vaginal opening, the medical device including a flexible member having a distal end portion with a closed end, a proximal end portion with an open end, and an elongate portion joining the proximal end portion and the distal end portion, wherein the distal end portion and the elongate portion contacts outer surfaces of vaginal walls and the proximal end portion resides out of the vaginal opening upon placement;

piercing the medical device at a desired location for conducting the implant surgery; and delivering a bodily implant within the patient's body through the pierced location formed in the medical device.

2. The method of claim 1, further comprising stretching the distal end portion and the elongate portion.

3. The method of claim 1, further comprising creating a bodily incision through the medical device.

4. The method of claim 3, further comprising closing the bodily incision.

5. The method of claim 1, further comprising removing the medical device from the body opening after completing the surgery.

\* \* \* \* \*